United States Patent [19]

Yoshikawa et al.

[11] Patent Number: 5,238,931
[45] Date of Patent: Aug. 24, 1993

[54] INFLAMMATORY BOWEL DISEASE PREVENTIVE AND CURATIVE AGENT CONTAINING ZINC L-CARNOSINE SALT AS ACTIVE INGREDIENT

[75] Inventors: Toshikazu Yoshikawa, Uji; Tomoyuki Yoneda, Kumagaya; Yasuhiro Nishimura, Fujiidera, all of Japan

[73] Assignees: Zeria Pharmaceutical Co., Ltd., Tokyo; Hamari Chemicals, Ltd., Osaka, both of Japan

[21] Appl. No.: 726,273

[22] Filed: Jul. 5, 1991

[30] Foreign Application Priority Data

Jul. 6, 1990 [JP] Japan .................................. 2-177560

[51] Int. Cl.$^5$ ............................................ A61K 31/555
[52] U.S. Cl. .................................... 514/184; 514/400; 514/867
[58] Field of Search .......................... 514/184, 400, 867

[56] References Cited

FOREIGN PATENT DOCUMENTS

| | | |
|---|---|---|
| 0303380 | 2/1989 | European Pat. Off. . |
| 0313654 | 5/1989 | European Pat. Off. . |
| WO91/04737 | 4/1991 | PCT Int'l Appl. . |
| 2144039 | 2/1985 | United Kingdom . |

OTHER PUBLICATIONS

Drugs of the Future, vol. 14, No. 12, 1989, pp. 1176–1177, "Z-103".
Gastroenterology, vol. 98, No. 5, May 12–18, 1990, part 2 of 2 parts, p. A94, M. Nakajima, et al., "Z-103, A New Antiulcer Agent, Inhibits Not Only Urease Activity But Also Campylobacter Pylori Growth".
Patent Abstracts of Japan, vol. 8, No. 122 (C-227) [1559], Jun. 8, 1984, & JP-A-59-33270, Feb. 23, 1984, H. Fujimura, et al., "Zinc Salt of Carnosine and Preparation Thereof".
Patent Abstracts of Japan, vol. 9, No. 112, (C-281) [1835], May 16, 1985, & JP-A-60-60-4172, Jan. 10, 1985, H. Fujimura, et al., "Zinc Hydroxide Salt of Carnosine and Its Preparation".
Patent Abstracts of Japan, vol. 15, No. 133 (C-820) [4661], Apr. 2, 1991 & JP-A-3-17022, Jan. 25, 1991, T. Yoshikawa, et al., "Remedy for Pancreatitis".
Akira Terano, "Mechanistic Aspects of Gastric Cytoprotection-A Review-, " Gastroenterologia Japonica, vol. 27, No. 2 (1992).
Robert D. Zipser, MD, "Mediators of Inflammation in Inflammatory Bowel Disease," Digestive Diseases and Sciences, vol. 33, No. 3, pp. 4S-5S (Mar. 1988 Supplement).

Primary Examiner—Leonard Schenkman
Attorney, Agent, or Firm—Oblon, Spivak, McClelland, Maier & Neustadt

[57] ABSTRACT

An agent for the prevention and treatment of inflammatory bowel disease (IBD) containing at least one of zinc L-carnosine salts and complexes as an active ingredient. A use of the zinc L-carnosine salts or complexes and a therapeutic method of IBD by using the same are also disclosed.

2 Claims, No Drawings

INFLAMMATORY BOWEL DISEASE PREVENTIVE AND CURATIVE AGENT CONTAINING ZINC L-CARNOSINE SALT AS ACTIVE INGREDIENT

BACKGROUND OF THE INVENTION i) Field of the Invention:

The present invention relates to inflammatory bowel disease (hereinafter referred to as IBD) preventive and curative agents containing a zinc L-carnosine salt or complex as an active ingredient, and a therapeutic method using the same.

ii) Description of the Background Art:

IBD is a term which means a disease with inflammation on an intestinal mucosa as a main place and inflammatory intestinal lesion due to a variety of causes, including ulcerative colitis from unknown causes, Crohn's disease and the like. Recently, these diseases have been increased, and therefore, designated as a research subject of the Special Disease Research Study Team of the Welfare Ministry in Japan. IBD is a chronic disease which repeats recrudescence and defervescence. The symptoms of IBD include mucous hemafecia or hemafecia repeated continuously or repeatedly, and an abnormal defecation such as diarrhea is observed.

As a cause of this disease, various theories such as infection theory, allergy theory, enzyme theory and the like have been presented. However, there is not established theory so far, and the cause is still unknown. In the meantime, autoimmunity theory is paid attention to since Broberger et al. reported that anticoli antibody was found from a patient's blood serum of this disease (see J. Exp. Med., Volume 115: pp. 13-26, 1962).

For the treatment of this disease, there has been employed two types of basic drugs which are salazosulfapyridine and adrenocortical steroid drugs. Further, an immunosuppressant such as azathioprine, metronidazole, antibiotics for preventing secondary infection are used, too. The salazosulfapyridine, a common preparation for the treatment of this disease is mostly decomposed into two metabolites of sulfapyridine and 5-aminosalicyclic acid by an action of enteric bacteria after oral dosage. It is considered that the salazosulfapyridine owes its effects to the 5-aminosalicyclic acid, and it seems that side-effects frequently observed are caused by the sulfapyridine of metabolite (see Khan et al., Lancet, p. 2892, 1977). Also, since the 5-aminosalicylic acid is unstable, and in effect, little amount of this substance reaches a colon when orally dosed, therapeutic effect is weak. As the side-effects of the salazosulfapyridine, nausea, vomiting, anorexia, exanthema, headache, hepatopathy, leukopenia, abnormal erythrocyte, proteinuria, diarrhea and the like are reported. Further, as the adrenocortical steroid drug, prednisolone is usually used in oral dosage, clysma, suppository, vein injection or the like with a strong side-effects such as gastric ulcer and caput femoris necrosis due to a long period of use.

Accordingly, a drug having strong IBD preventive and curative effects with reduced side-effects has been demanded.

Meanwhile, zinc L-carnosine salt is known to have a digestive ulcer therapeutic function (ssee Japanese Patent Application Laid-open (Kokai) No. 59-33270), preventive and therapeutic functions of hepatopathy (see Japanese Patent Application Laid-open (Kokai) No. 63-14728). However, it is neither taught or suggested that a zinc L-carnosine salt or complex has IBD preventive and curative functions, since the occurrence position, the occurrence mechanism and the therapeutic purpose are different.

SUMMARY OF THE INVENTION

Accordingly, it is an object of the present invention to provide an agent for the prevention and treatment of IBD containing at least one of zinc L-carnosine salts and complexes as an active ingredient in view of the aforementioned defects and drawbacks of the prior art.

It is another object of the present invention to provide a use of at least one of zinc L-carnosine salts and complexes as an agent for the prevention and treatment of IBD.

It is a further object of the present invention to provide a use of at least one of zinc L-carnosine salts and complexes for the prevention and treatment of IBD.

It is still another object of the present invention to provide a therapeutic method of IBD by dosing an effective amount of at least one of zinc L-carnosine salts and complexes to an IBD patient.

The above and other objects, features and advantages of the present invention will more fully appear from the following description.

DETAILED DESCRIPTION OF THE INVENTION AND PREFERRED EMBODIMENTS

According to the present invention, IBD preventive and curative drugs or agents contains at least one of zinc L-carnosine salts and complexes as an active ingredient.

The zinc L-carnosine salts or complexes are present in an amorphous or crystalline form, but there is no difference in the effect on the prevention and treatment of IBD. These two forms can be differentiated by, for instance, an observation by means of an electron microscope, infrared absorption spectra, X-ray diffraction patterns and the like.

The zinc L-carnosine salts or complexes can be prepared by reacting L-carnosine with a zinc salt and an alkali metal compound in water or in an organic solvent. The crystalline zinc L-carnosine salts or complexes can be prepared by reacting one mol of L-carnosine with 0.8 to 1.2 mol of a zinc salt and 1.6 to 2.4 mol of an alkali metal compound in an anhydrous or hydrous polar organic solvent at room temperature or under heat (see Japanese Patent Application Laid-open (Kokai) No. 64-42471).

As to the polar organic solvent, alcohols such as methanol, ethanol, propanol and the like, acetonitrile, dimethyl sulfoxide, N, N-dimethylformamide, tetrahydrofuran, acetone and the like can be used, and the same including approximately 50% by weight of water can be also used. Relating to the zinc salt, not only inorganic zinc salts but also organic zinc salts can be used. For example, for the former, zinc halides, zinc sulfate, zinc nitrate, zinc perchlorate and the like are given, and for the latter, zinc salts of carboxylic acids such as zinc acetate, zinc acetylacetonate and the like are given. Furthermore, any zinc salt capable of proceeding the reaction can be used. As regards the alkali metal compound, lithium hydroxide, potassium hydroxide, sodium hydroxide, potassium alcoholates, sodium alcoholates and the like can be used.

Further, the amorphous zinc L-carnosine salts or complexes can be prepared in the same manner as described above except that the water is used in place of the anhydrous or hydrous polar organic solvent.

Thus the obtained zinc L-carnosine salts or complexes can be mixed with auxiliary agents to obtain preparations for oral or parenteral dosage, and particularly oral dosage preparations are preferable. For the oral dosage preparations, the zinc L-carnosine salts or complexes can be combined with proper additives, for instance, excipients such as lactose, mannitol, corn starch, crystalline cellulose and the like, binders such as cellulose derivatives, acacia, gelatin and the like, disintegrants such as carboxymethylcellulose calcium and the like, and lubricants such as talc, magnesium stearate and the like to obtain tablets, powders, granules and capsules. Further, these solid preparations can be coated with a coating base such as hydroxypropylmethyl cellulose phthalate, hydroxypropylmethyl cellulose acetate succinate, cellulose acetate phthalate, methacrylate copolymer and the like to obtain enteric preparations. Furthermore, they can be dissolved in middle chain fatty acid triglyceride, safflower oil, soybean oil or polyethylene glycol 400 to prepare soft capsules. For the parenteral preparations, the zinc L-carnosine salts or complexes are combined with water, ethanol, glycerol and/or a surfactant of common use to obtain solutions for injection and also with a suppository base to obtain suppositories.

The dose of the preparations may differ depending on patient's age, weight, symptoms, therapeutic effects, administration route and period. Usually, in case of oral route, it is dosed with a range of 1 to 2000 mg/day, preferably 10 to 1000 mg/day, more preferably 10 to 200 mg/day in terms of zinc L-carnosine salt or complex one to three times a day.

According to the present invention, IBD preventive and curative drugs or agents containing at least one of zinc L-carnosine salt and complex as an active ingredient have excellent inhibiting or suppressing functions against the bleeding and ulcer of colonic mucosa, the hyperplasia of colon and the leukocyte humidity, and exhibit extremely low toxicity and weak side-effect. Hence, the drugs or agents of the present invention are very much useful for the prevention and treatment of IBD.

EXAMPLES

Having now generally described this invention, a further understanding can be obtained by reference to certain specific examples which are provided for the purposes of illustration only and are not intended to be limiting unless otherwise specified.

REFERENTIAL EXAMPLE 1

Preparation of crystalline zinc L-carnosine complex

In 100 ml of methanol, 3.51 g of sodium hydroxide was dissolved, and 9.96 g of L-carnosine was added to obtain a homogeneous solution. To this solution, a solution obtained by dissolving 9.67 g of zinc acetate.2H$_2$O into 145 ml of methanol was dropped over 30 minutes, while the solution was stirred, to gradually produce white precipitate therein. After finishing of the dropping, the solution was stirred for 2 hours and then left it overnight as was. The solution was filtered, and the precipitation was washed by 140 ml of water and then air-dried at 80° C. for 5 hours to obtain 12.4 g of white powdery crystals. The results of an analysis of the obtained material are as follows:

IR(KBr) cm$^{-1}$: 3292, 1626, 1563, 1389, 1262, 1230, 1117, 1060, 1030, 999, 982, 883, 787.

| Elementary analysis (as C$_9$H$_{12}$N$_4$O$_3$Zn): | | | | |
|---|---|---|---|---|
| | C | H | N | Zn |
| Calculated (%): | 37.33 | 4.18 | 19.35 | 22.53 |
| Measured (%): | 37.07 | 4.27 | 19.06 | 22.50 |

| Lattice plane interval: (d; angstrom) | Relative intensity: (%; I/Io) |
|---|---|
| 11.87 | 26 |
| 7.54 | 28 |
| 5.97 | 43 |
| 5.55 | 27 |
| 5.26 | 30 |
| 4.52 | 51 |
| 3.96 | 100 |
| 3.56 | 19 |
| 3.24 | 29 |
| 2.97 | 19 |
| 2.79 | 17 |
| 2.68 | 22 |
| 2.58 | 21 |
| 2.38 | 25 |
| 2.10 | 13 |
| 1.97 | 14 |
| 1.88 | 15 |
| 1.84 | 14 |
| 1.69 | 10 |
| 1.57 | 9 |
| 1.55 | 9 |
| 1.53 | 10 |

TEST EXAMPLE 1

Action against IBD

Action of the crystalline zinc L-carnosine complex against IBD was confirmed by using an experimental ulcerative colitis model established by the administration of dextran sodium sulfate (see Ohkusa, Bulletin of Gastroenterology Society Japan, Volume 82: pp. 1327-1336, 1985) or trinitrobenzenesulfonic acid (see Morriset al., Gastroenterology, Volume 96: pp. 795-803, 1989).

(1) Ulcerative colitis model induced by dextran sodium sulfate:

Several groups of rats, each group consisting of 12 male Sprague-Dawley rats weighing 190-210 g, were allowed to freely take 5% dextran sodium sulfate aqueous solution from a water feed bottle every day to make ulcerative colitis. After 7 days from the start of the dosage of the dextran sodium sulfate, the colons of the rats were enucleated, and intraluminal hemoglobin amount was measured by cyanmethemoglobin method (see Van Kampen, E. J. et al., Clin. Chim. Acta, Volume 6: pp. 538-544, 1961) to define it as an index of digestive tract bleeding. The crystalline zinc L-carnosine complex as a drug was orally dosed to the rats every day after the start of the dextran sodium sulfate dosage. Also, salazosulfapyridine as a comparative drug was orally dosed in the same manner as described above. The drugs were orally dosed to a comparative group as suspended in a physiological saline. The results of the hemoglobin amount in the colon intralumina are shown in Table 1.

TABLE 1

| Drug | Dose (mg/kg) | Intraluminal hemoglobin amount (mg/rat) |
|---|---|---|
| Comparative group | | 18.6 ± 5.4 |
| Zinc L-carnosine complex | 10 | 18.2 ± 4.3 |
| | 30 | 6.7 ± 1.1*) |
| | 100 | 3.3 ± 0.6*) |
| Salazosulfa-pyridine | 100 | 23.1 ± 6.7 |

*)$p<0.05$

As apparent from Table 1, the zinc L-carnosine complex significantly suppressed the hemoglobin amount (digestive tract bleeding) appeared in the lumina of the rats in proportion to the dose of the zinc L-carnosine complex in the ulcerative colitis induced by dextran sodium sulfate, whereas the salazosulfapyridine as the comparative drug did not exhibit such action.

(2) Ulcerative colitis model induced by trinitrobenzenesulfonic acid:

Several groups of rats, each group consisting of 12 male Sprague-Dawley rats having a weight of 190 to 210 g, were anesthetized by ether, and a rubber catheter having an internal radius of 2 mm was inserted 8 cm into each rat from its rectum and 0.25 ml of an aqueous solution obtained by dissolving 120 mg/ml of trinitrobenzenesulfonic acid in 50% ethanol was injected to make ulcerative colitis. After 5 days from the start of the dosage of the trinitrobenzenesulfonic acid, the colons of the rats were enucleated, and after cutting it open, degree of a caused ulcer was measured by the above-described method of Morris et al. (Gastroenterology, Volume 96: pp. 795-803, 1989). As an index of hyperplasia and edema of the colon, a wet weight of the colon at 10 cm from the rectum was measured. Further, as an index of leukocyte humidity, myeloperoxidase (MPO) activity in the colon was measured by a method according to Granger et al. (Gastroenterology, Volume 94: pp. 673-681, 1988). The crystalline zinc L-carnosine complex as a drug was orally dosed to the rats every day after the start of the trinitrobenzenesulfonic acid dosage. Also, salazosulfapyridine as a comparative drug was orally dosed in the same manner as described above. The drugs suspended in the physiological saline were orally dosed to a comparative group. The injury indexes caused on colonic mucosa are shown in Table 2. The colon wet weights are shown in Table 3, and the MPO activities in the colons are shown in Table 4.

TABLE 2

| Drug | Dose (mg/kg) | Mucosa injury index |
|---|---|---|
| Comparative group | | 4.0 ± 0.4 |
| Zinc L-carnosine complex | 10 | 2.7 ± 0.4*) |
| | 30 | 2.5 ± 0.3*) |
| Salazosulfa-pyridine | 100 | 4.2 ± 0.2 |

*)$p<0.05$

TABLE 3

| Drug | Dose (mg/kg) | Colon wet weight (g/10 cm) |
|---|---|---|
| Comparative group | | 1.71 ± 0.20 |
| Zinc L-carnosine complex | 10 | 1.09 ± 0.03**) |
| | 30 | 1.13 ± 0.06**) |
| Salazosulfa-pyridine | 100 | 1.42 ± 0.20 |

**)$p<0.001$

TABLE 4

| Drug | Dose (mg/kg) | Colon MPO activity (U/g wet weight) |
|---|---|---|
| Comparative group | | 297 ± 48 |
| Zinc L-carnosine complex | 10 | 104 ± 8***) |
| | 30 | 153 ± 13**) |
| Salazosulfa-pyridine | 100 | 175 ± 43 |

**)$p<0.01$,
***)$p<0.001$

As clear from Tables 2 to 4, the zinc L-carnosine complex significantly suppressed the ulcer index appeared on the colonic mucosa, the colon wet weight (hyperplasia and edema) and the colon MPO activity (leukocyte humidity) in the ulcerative colitis induced by the trinitrobenzenesulfonic acid, and its action was stronger than that of the salazosulfapyridine.

TEST EXAMPLE 2

Toxicity test

To each group of 10 female and male Wistar rats having a weight of 150 to 200 g, 10 g of crystalline zinc L-carnosine complex per one kg of rat was orally dosed for each, and the rats were observed for 7 days. No death was noticed. Further, diarrhea was not observed in any rat at all.

PREPARATION EXAMPLE

| | |
|---|---|
| Crystalline zinc L-carnosine complex | 50 g |
| Lactose | 315 g |
| Corn starch | 125 g |
| Crystalline cellulose | 25 g |

These components were uniformly mixed, and 200 ml of 7.5% hydroxypropyl cellulose aqueous solution was added to the mixture. Then, the mixture was granulated by an extruder granulator using a screen having a diameter of 0.5 mm, and the formed particles were immediately processed by a marumerizer to adjust the grain size. The prepared particles were dried to obtain granules.

PREPARATION EXAMPLE 2

| | |
|---|---|
| Crystalline zinc L-carnosine complex | 20 g |
| Lactose | 100 g |
| Corn starch | 36 g |
| Crystalline cellulose | 30 g |
| Calcium carboxymethyl cellulose | 10 g |
| Magnesium stearate | 4 g |

These components were uniformly mixed, and the mixture was pounded with a pestle having a diameter of 7.5 mm in a tabletting machine to prepare tablets each weighing 200 mg.

Then, the obtained tablets were splay-coated with following composition to have a film of 10 mg per each tablet over the tablets to obtain enteric-coated tablets.

| Coating liquid composition: | |
| --- | --- |
| Hydroxypropylmethylcellulose phthalate | 8.0 (W/W) % |
| Glycerol fatty acid ester | 0.4 (W/W) % |
| Methylene chloride | 50.0 (W/W) % |
| White beeswax | 0.1 (W/W) % |
| Isopropanol | 41.5 (W/W) % |

PREPARATION EXAMPLE 3

| | |
| --- | --- |
| Amorphous zinc L-carnosine complex | 7 g |
| Soybean phospholipid | 3 g |
| Witepzol H-12 (trademark) | 50 g |
| Witepzol H-15 (trademark) | 200 g |

These components were uniformly mixed under heat, and the mixture was poured into a mold. Then, the mold was cooled to prepare suppositories of about 2.6 g each.

PREPARATION EXAMPLE 4

| | |
| --- | --- |
| Amorphous zinc L-carnosine complex | 10 g |
| Acacia | 1050 g |
| Benzoic acid | 6 g |

These components were uniformly mixed under heat, and a proper amount of purified water was added to the mixture to make a 3000 ml solution. 30 ml of the obtained mixture solution was placed in a bottle and was sealed to prepare clysters.

In the above-described embodiments, although either zinc L-carnosine salt or complex is used, both the zinc L-carnosine salt and complex can be used together.

What is claimed is:

1. A method of treating inflammatory bowel disease, comprising administering an effective amount of zinc L-carnosine in a pharmaceutically acceptable carrier to a patient in need thereof.

2. The method of claim 1, wherein said zinc L-carnosine is administered orally.

* * * * *